US 6,669,557 B2

(12) United States Patent
Adams et al.

(10) Patent No.: US 6,669,557 B2
(45) Date of Patent: Dec. 30, 2003

(54) APPARATUS FOR MEASURING PARAMETERS OF MATERIAL

(75) Inventors: Brian T. Adams, Pleasant Hill, IL (US); Thomas Karlmann, Hoffman Estates, IL (US); George H. Hale, Naperville, IL (US); William L. Schubert, Downers Grove, IL (US)

(73) Assignee: Case, LLC, Racine, WI (US)

( * ) Notice: Subject to any disclaimer, the term of this patent is extended or adjusted under 35 U.S.C. 154(b) by 0 days.

(21) Appl. No.: 10/298,131

(22) Filed: Nov. 15, 2002

(65) Prior Publication Data

US 2003/0076118 A1 Apr. 24, 2003

Related U.S. Application Data

(60) Division of application No. 09/825,498, filed on Apr. 3, 2001, now Pat. No. 6,489,784, which is a division of application No. 09/027,179, filed on Feb. 23, 1998, now Pat. No. 6,242,927, which is a continuation-in-part of application No. 08/835,610, filed on Apr. 9, 1997, now Pat. No. 6,121,782.

(51) Int. Cl.$^7$ .......................... A01D 75/18; A01F 12/16; A01F 21/00
(52) U.S. Cl. ............................................. 460/7; 324/664
(58) Field of Search ................................. 324/664, 663, 324/667, 674, 681, 686, 689; 460/7, 4–5

(56) References Cited

U.S. PATENT DOCUMENTS

| 4,058,766 | A |   | 11/1977 | Vogel et al. ................. 324/659 |
|---|---|---|---|---|
| 4,228,393 | A |   | 10/1980 | Pile ............................ 324/667 |
| 4,370,611 | A |   | 1/1983 | Gregory et al. ............. 324/663 |
| 4,433,286 | A |   | 2/1984 | Capots et al. ............... 324/663 |
| 4,881,025 | A |   | 11/1989 | Gregory ...................... 324/672 |
| 4,991,128 | A |   | 2/1991 | Evans et al. .................. 702/77 |
| 5,078,645 | A | * | 1/1992 | Bohman et al. ............... 460/2 |
| 5,106,339 | A | * | 4/1992 | Braun et al. .................. 460/7 |
| 5,166,679 | A |   | 11/1992 | Vranish et al. .............. 324/687 |
| 5,214,388 | A |   | 5/1993 | Vranish et al. .............. 324/662 |
| 5,351,558 | A |   | 10/1994 | Horn et al. ............... 73/861.08 |
| 5,363,051 | A |   | 11/1994 | Jenstrom et al. ............. 324/661 |
| 5,373,245 | A |   | 12/1994 | Vranish ....................... 324/662 |
| 5,442,347 | A |   | 8/1995 | Vranish ....................... 324/686 |
| 5,487,702 | A |   | 1/1996 | Campbell et al. ............... 460/7 |
| 5,515,001 | A |   | 5/1996 | Vranish .................... 324/123 C |
| 5,521,515 | A |   | 5/1996 | Campbell .................... 324/662 |
| 6,121,782 | A |   | 9/2000 | Adams et al. ............... 324/689 |
| 6,146,268 | A | * | 11/2000 | Behnke et al. ................. 460/4 |
| 6,242,927 | B1 |   | 6/2001 | Adams et al. ............... 324/664 |

OTHER PUBLICATIONS

US 4,336,493, 6/1982, Gregory et al. (withdrawn)

\* cited by examiner

*Primary Examiner*—Árpád Fábián Kovács
(74) *Attorney, Agent, or Firm*—Rebecca Henkel

(57) ABSTRACT

An apparatus for measuring at least one parameter of material and generating multiple frequency signals having frequencies selectable by control signals, combining the multiple frequency signals into a combined frequency signal having multiple frequency components, and applying the combined frequency signal as an excitation signal to a sensing element. The frequency response of the material is determined at each of the multiple frequencies using output signals from the sensing element, and a frequency analysis is performed to determine the parameters of the material. The sensing element may include a capaciflector sensor located non-intrusively along the surface of a conveyor. However, other sensing elements such as capacitive, resistive and inductive elements may be used. The parameters being measured may include mass flow rate and moisture content. The apparatus includes a frequency generating circuit for generating a frequency signal having multiple frequency components, a sensing circuit which applies the frequency signal as an excitation signal to a sensing element, a signal conditioning circuit which determines the frequency response of the material at the multiple frequencies based upon output signals from the sensing element, and a signal processing circuit for performing a frequency analysis. The apparatus may be used to measure parameters of material being moved by a vehicle-mounted conveyor. A pink or white noise generator may be used for the frequency generating circuit.

4 Claims, 7 Drawing Sheets

APPARATUS FOR MEASURING PARAMETERS OF MATERIAL

REFERENCE TO RELATED APPLICATIONS

This is a Divisional of application Ser. No. 09/825,498, filed Apr. 3, 2001 and issued on Dec. 3, 2002 as U.S. Pat. No. 6,489,784 which is a Divisional of application Ser. No. 09/027,179, filed Feb. 23, 1998 and issued on Jun. 5, 2001 as U.S. Pat No. 6,242,927 which is continuation-in-part of application Ser. No. 08/835,610, filed on Apr. 9, 1997 and issued on Sep. 19, 2000 as U.S. Pat. No. 6,121,782.

FIELD OF THE INVENTION

The present invention relates generally to the field of measuring parameters of material. More particularly, the invention relates to a method and an apparatus for measuring parameters of a material by driving a sensing element with multiple simultaneous frequency signals, generating signals responsive to the frequency response of the material at each frequency, and processing the generated signals to determine the parameters of the material.

BACKGROUND OF THE INVENTION

Various mobile and stationary machine systems use conveyors for moving bulk materials from place to place. Different types of conveyors are known, such as belt conveyors including endless canvas, rubber or metal belts which support the material being moved and are pulled over pulleys or rollers, chain or cable conveyors which include chains or cables adapted to pull plates, buckets or containers loaded or filled with material being moved, and auger or screw conveyors which include a helix formed about a turning shaft for moving material through a tube.

Mobile machine systems which use conveyors include various types of agricultural vehicles and construction equipment. Combines, for example, typically include a clean grain elevator for moving material up to a delivery auger, a delivery auger for moving the clean grain into the grain bin, a tailings auger for moving tailings to the tailings elevator to be returned to the threshing system of the combine, and an unloading auger for moving material from the grain bin to a transport device. Other examples include cotton pickers having a conveyor for moving cotton into storage bins, planters having a conveyor for moving seeds or fertilizer, and forage harvesters having a conveyor to move foraged material. Some conveyors include pneumatic delivery systems which are used, for example, to deliver seed from a seed bin to a planter or to convey forage from a forage harvester to a wagon. Stationary systems using conveyors include, for example, grain elevators using a conveyor including a driven chain which pulls paddles loaded with grain.

The machine systems described above may include real-time sensors and systems for measuring or monitoring parameters of material moved by the conveyors. These sensed parameters may include, for example, the yield or mass flow rate of material being moved by the conveyor, or the moisture content of the material. For example, yield and moisture sensors may be mounted to a grain auger of a combine to measure the mass flow rate and moisture content of grain flowing through the auger.

Known systems for measuring moisture may include capacitive sensors mounted in or on a fin which extends into the flow of material to measure the capacitance of the material. These systems extend into the flow of material so that the sensors can detect moisture despite their limited range. However, the intrusion into the flow of materials may cause certain materials, such as plant residue or sap, to build up on the sensors as contact is made with material being moved. The resulting build-up can cause the sensors to give inaccurate or erroneous readings. In addition, the intrusion of the sensors into the material may restrict or interrupt the flow of material, and the exposed fins and sensors are subject to mechanical wear and breakage.

Other measuring systems use capacitive sensors in a test cell which receives a small portion of the material flow diverted from the main flow. Such systems, however, require additional components and structures to divert the flow of material from the main flow and for the test cell, thereby increasing cost and decreasing reliability. Such systems may also suffer from build-up on the sensors since the material makes contact with the sensors.

Known sensors used to measure certain parameters of material being moved, such as yield or mass flow rate, may contain radioactive isotopes. These sensors may be subject to regulation concerning their sale and use since they are radioactive sources, thereby subjecting the user to the increased costs and paperwork associated with regulation compliance. The user is also exposed to the costs and risks generally associated with the use and management of radioactive sources. Other yield sensors generate signals when harvested grain hits a plate, the signals depending on both the amount of grain hitting the plate and the force at which the grain hits. These sensors may be inappropriate for measuring parameters of certain non-granular materials, such as forage, and may be difficult to integrate into a particular system.

Another problem with known systems for measuring parameters of a material includes the limited frequency response of such systems. Certain parameters of a material, such as type, mass flow rate, moisture content, density or other parameters, can be identified or measured by driving a sensing element with different frequencies and measuring the response of the material to each frequency. For example, one measuring system which uses a capacitive sensor in a test cell includes three fixed frequency generators which generate three fixed frequency signals and a multiplexer which sequentially applies the frequency signals to the sensor. The response at each frequency is then measured. This system, however, may be unable to provide required resolution over a given frequency range because of the fixed frequency signals. Moreover, expansion of this system to include a sufficient number of frequency generators to provide the required resolution over a given frequency range may be impractical because of the high number of frequency generators needed. Another measuring system includes a sweeping frequency oscillator which drives a capaciflector sensor. This latter system is able to generate more frequencies than the former system. However, when a dynamic system is being measured, the use of swept frequencies may introduce errors because the dynamic system may change over the time required to sweep the frequency signals.

SUMMARY OF INVENTION

Accordingly, the present invention provides an improved method and apparatus for measuring parameters of material. The parameters which can be measured include material type, moisture content, mass flow rate, density and other parameters. Parameters are measured by determining the frequency response of the material to multiple simultaneous frequencies. The frequency response can be determined over a wide frequency range with required resolutions without the need for a large number of frequency generators. The parameters are accurately measured even in dynamic systems wherein the values change over time. Material can be measured in test cells, or while being moved by conveyors such as augers, elevators or pneumatic conveyors. Different types of sensing elements can be used such as capacitive, capaciflector, resistive or inductive sensing elements.

One embodiment of the invention relates to a method for measuring at least one parameter of material including the steps of generating a plurality of frequency control signals corresponding to a plurality of frequencies, generating a plurality of frequency signals having frequencies selectable by the respective frequency control signals, combining the frequency signals to generate a combined frequency signal having a plurality of frequency components, applying the combined frequency signal as an excitation signal to a sensing element coupled to the material being measured, determining the frequency response of the material at each of the frequencies based upon output signals from the sensing element, and analyzing the frequency response of the material to determine the at least one parameter.

Another embodiment of the invention relates to an apparatus for measuring at least one parameter of material including a frequency generating circuit configured to generate a combined frequency signal having a plurality of frequency components selected in response to a plurality of frequency control signals, a sensing circuit coupled to the frequency generating circuit and including a sensing element coupled to the material being measured, wherein the combined frequency signal is applied as an excitation signal to the sensing element and the sensing element generates output signals based upon the frequency response of the material at each of the frequencies, a signal conditioning circuit coupled to the sensing circuit and configured to determine the frequency response of the material at each of the frequencies based upon the output signals from the sensing element, and a signal processing circuit to analyze the frequency response of the material to determine the at least one parameter of the material.

Another embodiment of the invention relates to a work vehicle including a support structure for supporting components of the work vehicle, a plurality of wheels coupled to the support structure to move the work vehicle on a surface, at least one of the wheels being powered to move the work vehicle along the surface, and at least one conveyor to move material from a first location to a second location on the work vehicle. The work vehicle further includes a frequency generating circuit configured to generate a combined frequency signal having a plurality of frequency components selected in response to a plurality of frequency control signals, a sensing circuit coupled to the frequency generating circuit and including a sensing element coupled to the at least one conveyor, wherein the combined frequency signal is applied as an excitation signal to the sensing element and the sensing element generates output signals based upon the frequency response of the material being moved at each of the frequencies, a signal conditioning circuit coupled to the sensing circuit and configured to determine the frequency response of the material at each of the frequencies based upon the output signals from the sensing element, and a signal processing circuit configured to analyze the frequency response of the material to determine the at least one parameter of the material.

Another embodiment of the invention includes an apparatus for measuring at least one parameter of material. The apparatus includes a noise generating circuit configured to generate a noise signal having a substantially even power spectrum across at least a range of frequencies, a sensing circuit coupled to the noise generating circuit and including a sensing element coupled to the material being measured, wherein the noise signal is applied as an excitation signal to the sensing element and the sensing element generates output signals based upon the frequency response of the material, a signal conditioning circuit coupled to the sensing circuit and configured to determine the frequency response of the material at multiple frequencies based upon the output signals from the sensing element, and a signal processing circuit configured to analyze the frequency response of the material to determine the at least one parameter of the material.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF THE PREFERRED EMBODIMENTS

Before proceeding to the Detailed Description, a general comment can be made about the applicability and scope of the invention. While the following discussion makes specific reference to a method and apparatus to measure parameters of plant material moved by conveyors on an agricultural harvesting vehicle, it should be understood that the present invention is more generally applicable to a method and apparatus for measuring parameters of any type of material in general. Thus, a system employing the elements recited in the appended claims, though used in other applications, is equally within the intended scope of the invention.

Figure 1:
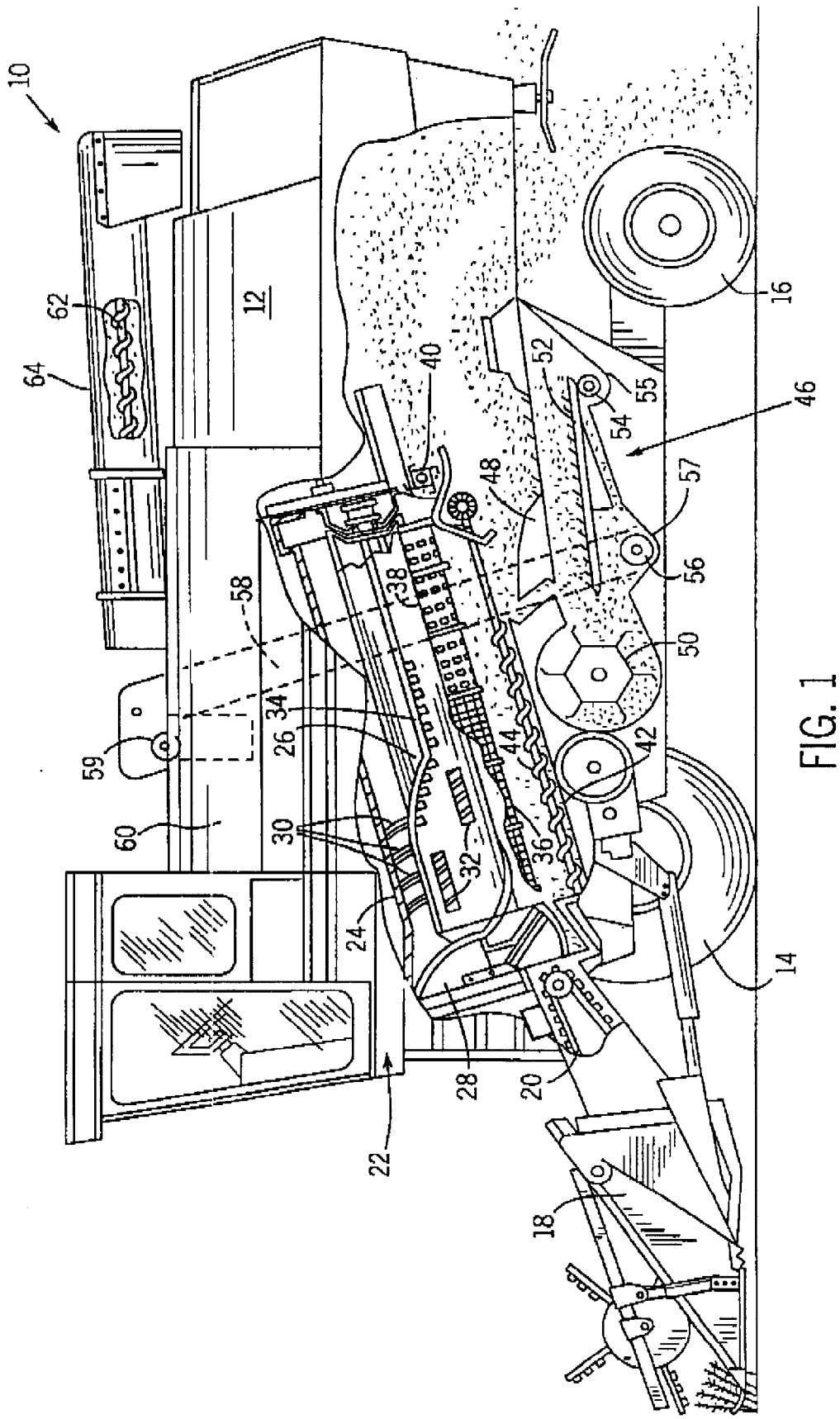
FIG. 1 illustrates an agricultural harvesting vehicle including augers and elevators for conveying harvested plant material.

Referring to FIG. 1, a method and apparatus for measuring parameters of material moved by a conveyor are used, for example, by an agricultural harvesting vehicle 10 (e.g., a combine). Vehicle 10 includes a main body 12 supported by front drive wheels 14 to propel the vehicle, and rear steerable wheels 16 which may be unpowered or powered. Alternatively, a tracked propulsion system may propel vehicle 10. A tool or implement 18 (e.g., a header) is movably coupled to the front of vehicle 10 to sever crop (e.g., wheat, corn) being harvested. However, other types of agricultural and construction equipment vehicles use other types of tools (e.g., row units, fertilizer spreaders, shovels, buckets) to transport bulk material in either direction between the vehicle and the ground or surface. The severed plant material is fed by a feeder 20 to an axial threshing and separating assembly 22 including a generally cylindrical casing 24 and rotor 26 mounted for rotation therein. A front-mounted impeller 28 on rotor 26 drives the material rearwardly, and the material is impelled helically about rotor 26 as rotor 26 rotates and cooperates with spiral vanes 30 located on an upper surface of casing 24.

As the plant material moves rearwardly, a plurality of rasp bars 32 and transport bars 34 mounted on rotor 26 cooperate with a concave 36 and a grate 38, respectively, to thresh the crop material such that most of the grain is separated and impelled outwardly through the concave and grate. Straw and other waste materials are impelled rearwardly from casing 24 by a rotary beater 40. The separated grain falls onto a grain pan 42 and is conveyed rearwardly by an auger 44 for cleaning and collection. Grain pan 42 is a stationary member which supports the material moved by auger 44.

A cleaning and collection system 46 separates grain from the waste materials (e.g., chaff, tailings and other wastes) received from auger 44 and grate 38. System 46 includes a chaffer sieve 48, a cleaning fan 50, a grain sieve 52, a tailings auger 54 and a clean grain auger 56. Stationary members 55 and 57 support the material being moved by augers 54 and 56, respectively. Chaffer sieve 48 separates the chaff from the grain and tailings by reciprocating in the fore-and-aft direction. Chaff unable to pass through openings in sieve 48 is carried away by an upward and rearward airflow from cleaning fan 50. Grain and tailings passing through sieve 48 fall onto grain sieve 52 and are separated by reciprocations of the grain sieve. Tailings unable to pass through the openings in sieve 52 are moved rearwardly onto tailings auger 54 for disposal. Clean grain passing through both sieves 48 and 52 is collected by clean grain auger 56 and conveyed by a clean grain elevator 58 and a delivery auger 59 to a grain tank 60. An unloading auger 62 within an unloading tube 64 is used to offload the harvested grain to a transport device (not shown). Power for the above-described crop processors is provided by the vehicle's engine (not shown).

Vehicle 10 is preferably similar to the 2100 Series of axial-flow combines made by Case Corporation except that any or all of the plant material conveyors are equipped with sensor assemblies 112 as disclosed herein. Vehicle 10, however, could also include other conventional or axial-flow combines, cotton harvesters such as the model 2155 and 2555 cotton harvesters made by Case Corporation, sugar-cane harvesters, hay balers, or other agricultural harvesting vehicles. A sensor assembly 112 is located on a surface of any or all of augers 44, 54, 56, 59, 62, and an auger running across the length of header 18, and elevator 58 or feeder 20, to measure parameters of the plant material being conveyed. As explained below, the parameters can include the mass flow rate and moisture content of the material. The type of material may also be determined. Signals from sensor assemblies 112 can also be used to determine the rotational speeds of the auger screws in augers 44, 54, 56, 59 and 62, and the speed of elevator 58 and feeder 20.

Figure 2:
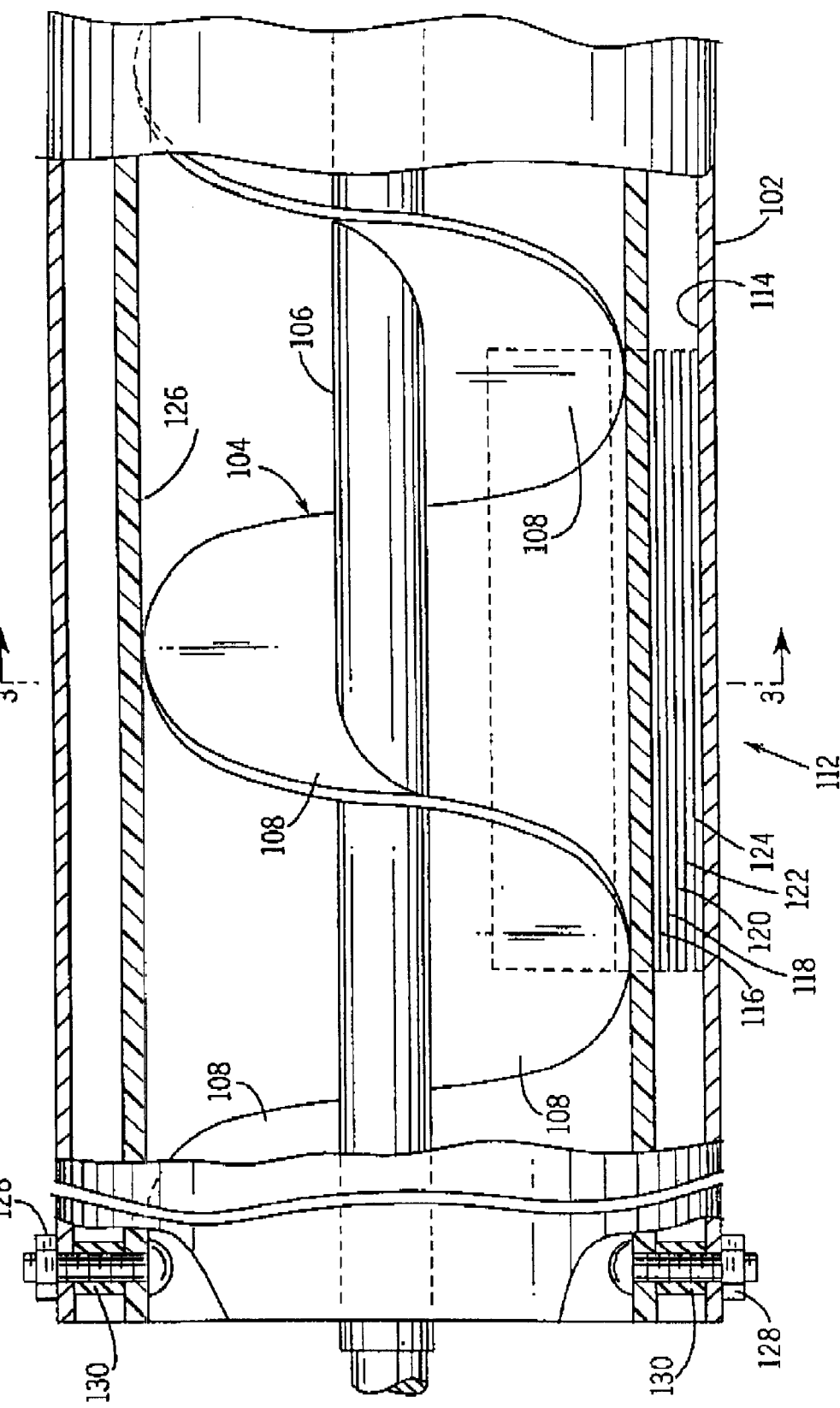
FIG. 2 is a partial cross-sectional view of an auger equipped with a non-intrusive sensor assembly located along a surface of the auger and configured to measure mass flow rate and moisture content of material moved by the auger.
Figure 3:
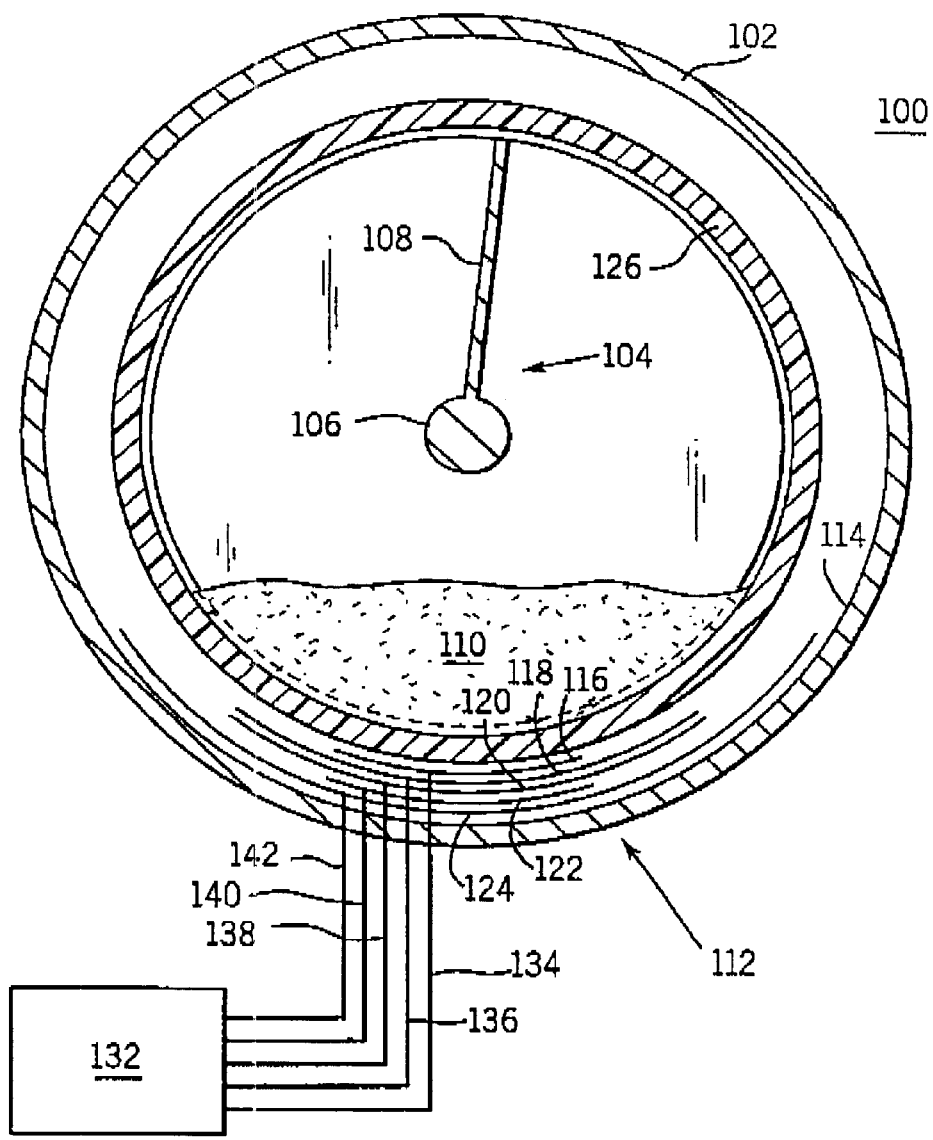
FIG. 3 is a sectional view of the auger equipped with a non-intrusive sensor assembly taken along line 3—3 in FIG. 2 which includes a block diagram showing the coupling between the sensor assembly and associated electronic circuits.

Referring to FIGS. 2 and 3, an auger 100 includes a housing 102 and a screw 104 extending longitudinally and axially through housing 102. Housing 102 can include a cylindrical tube such as tube 64 which encloses a screw 104 such as the screw of auger 59. Alternatively, housing 102 may be a stationary member (e.g., flat or curved plate) running along the length of screw 104 but not enclosing screw 104 (e.g., grain pan 42, member 55 or member 57). Screw 104 includes a shaft 106 and helical members 108 formed about shaft 106. Shaft 106 is coupled to a power source (e.g., the vehicle's engine) through an appropriate gearing or transmission such that shaft 106 rotates within housing 102. As shaft 106 rotates, helical members 108 advance loose or bulk material 110 such as grain, seed, forage, fertilizer, soil, etc. through housing 102 to move or convey the bulk material.

A sensor assembly 112 is located along an inner surface of housing 102. Sensor assembly 112 is a non-intrusive sensor assembly which does not extend into the flow of material moved through auger 100, and does not interfere with rotation of screw 104. Sensor assembly 112 is preferably a capacitive-type sensor assembly with a structure related to a capaciflector proximity sensor assembly as described in U.S. Pat. No. 5,166,679, incorporated herein by reference. Thus, sensor assembly 112 is referred to as a capaciflector sensor assembly. The sensor assembly described in the '679 patent detects proximity between a machine and an object with improved range and sensitivity as compared to other capacitance proximity sensors. These characteristics are provided by a shield conductor located between the sensor probe and a reference plane. Sensor electronics drive the shield with the same excitation voltage as the sensor probe to block the direct capacitance between the sensor probe and the reference plane. Since the electric field lines of the sensor probe are effectively focused away from the shield, a larger change in signal occurs when an object intrudes in front of the sensor as compared with traditional sensors.

Sensor assembly 12 preferably includes five layers of electrical conductors located along an inner surface 114 of housing 102. Starting with the conductor closest to material 110, sensor assembly 112 includes a sensor 116, a sensor shield 118, a compensation sensor shield 120, a compensation sensor 122 and a reference plane 124. As shown in FIG. 3, sensor shield 118 is preferably larger than sensor 116 to reduce parasitic capacitance between sensor 116 and plane 124. Compensation sensor 122 provides a signal used for environmental compensation of the sensed parameter of material 110, and compensation sensor shield 120 is larger than compensation sensor 122 to provide effective shielding. Reference conductor 124 provides a clean ground plane. Alternatively, if made of conductive material, housing 102 can form the reference plane provided the electrical noise level is low enough. Sensor assembly 112 may be located such that sensor assembly 112 is consistently covered with material 110.

Conductors 116–124 are preferably made from strips of conductive material such as aluminum or copper, but can be made in other shapes and using other materials. In one embodiment, conductors 116–124 are made from strips of copper foil which can easily be made to conform to the contours of housing 102 regardless of the shape of housing 102 (e.g., a tube, a plane or another shape). An insulator (not shown) such as a polyimide material (e.g., "KAPTON") provides insulation between adjacent conductors 116–124, and between reference plane 124 and housing 102. Sensor assembly 112 may also be fabricated using other methods of making conductive or non-conductive layers which are known to people of skill in the art.

A cover 126 is preferably placed over sensor 116 to separate sensor assembly 112 from material 110 flowing through auger 100. Cover 126 is preferably a low-friction plastic plate, and may comprise a high molecular weight polyethylene. However, cover 126 may be made from other materials having a low dielectric value such that cover 126 is transparent to sensor assembly 112. Cover 126 and housing 102 may be attached together using nut and bolt arrangements 128, with optional spacers 130 used to separate cover 126 from housing 102. Cover 126 may also comprise a coating (e.g., a urethane coating) cast over sensor assembly 112, or may be formed by a variety of methods known to people of skill in the art.

Sensor assembly 112 operates by detecting the capacitance of sensor 116 relative to reference plane 124. Sensor 116 forms a first electrode of a sensor capacitor and material 110 forms a second electrode of the sensor capacitor. The capacitance of this sensor capacitor depends on the dielectric value of material 110 moving through housing 102. This value, in turn, depends on the dielectric of the material that is influenced by factors such as the mass of material in auger 100, the moisture content of the material, and the type of material. Environmental compensation is provided by signals generated by compensation sensor 122.

Conductors 116–124 of sensor assembly 112 are coupled to electronic circuits 132 via electrical conductors 134–142, respectively. Electronic circuits 132 are described below in relation to FIG. 5.

Other configurations of sensor assembly 112 may be used. For example, the dimensions of conductors 116–124 may be changed in either or both directions, and sensor assembly 112 may encircle the entire circumference of housing 102 to form a tube. Sensor assembly 112 may have a planar shape for an auger (e.g., auger 44) which moves material over a planar member (e.g., grain pan 42).

Figure 4:
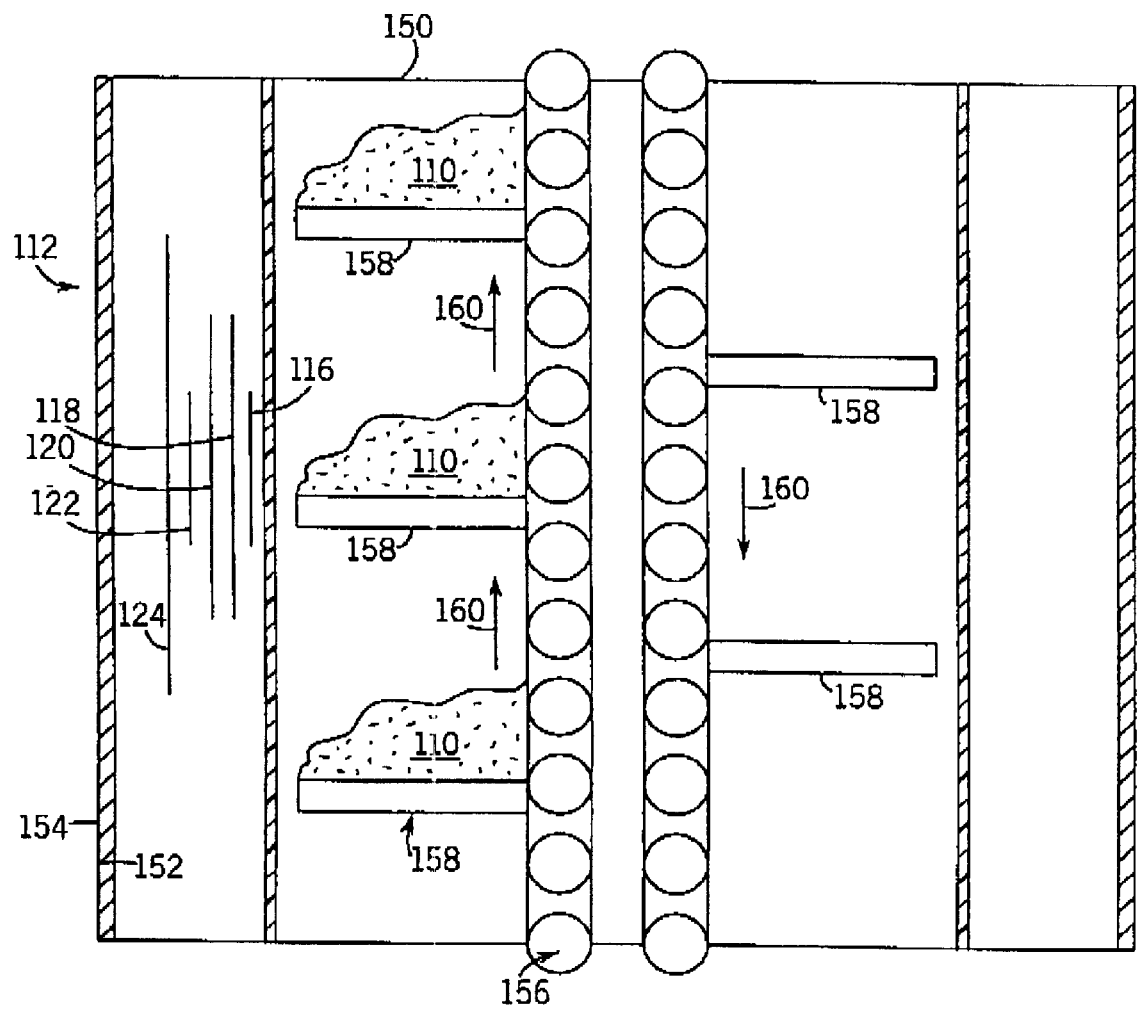
FIG. 4 is a block diagram showing an elevator equipped with a non-intrusive sensor assembly such as shown in FIG. 3 located along a surface of the elevator and configured to measure mass flow rate and moisture content of material moved by the elevator.

Referring to FIG. 4, an elevator conveyor 150 such as clean grain elevator 58 is equipped with non-intrusive sensor assembly 112 located along an inner surface 152 of elevator housing 154. Cover 126 is placed over sensor 116 to separate sensor assembly 112 from moving members within elevator 150 which include a belt or chain 156 and fighting or paddles 158 attached to chain 156. Power from, for example, the engine of vehicle 10 moves chain 156 in an endless loop in the direction of arrows 160. Paddles 158 pick up a volume of bulk material 110 and convey the material upward past sensor assembly 112. Sensor assembly 112 generates signals responsive to the mass flow rate, moisture content and type of material 110. Further, the generated signals are responsive to the movement of paddles 158. A similar arrangement is used to locate sensor assembly 112 along the bottom surface of feeder 20. Such an arrangement is used to measure the mass of material flowing through the combine.

Figure 5:
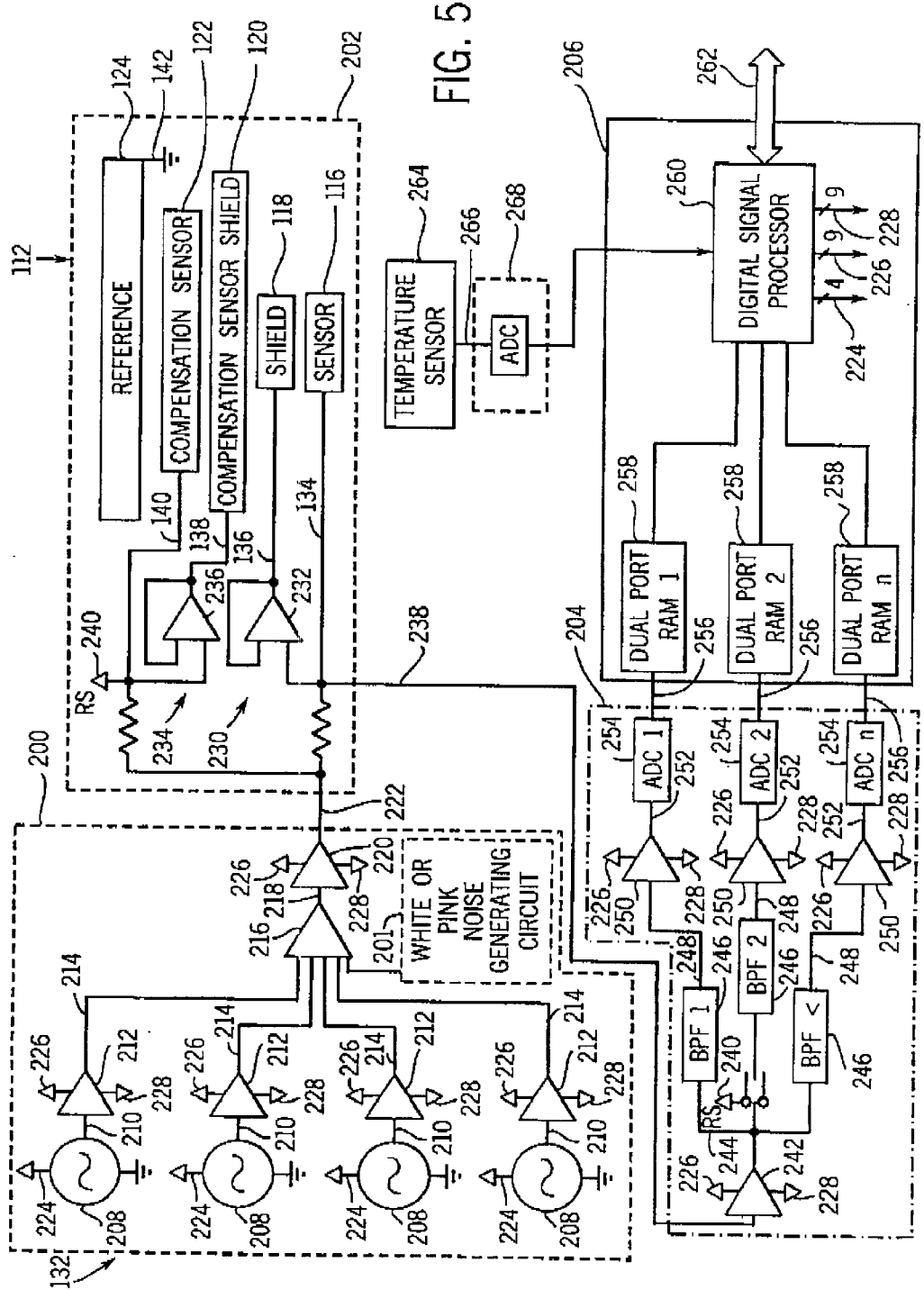
FIG. 5 is an electrical schematic diagram which represents the sensor assembly and associated electronic circuits of FIG. 3 wherein the electronic circuits drive the sensor assembly, generate signals responsive to the dielectric value of the material, and process the signals into values representing parameters of the material.

Referring to FIG. 5, electronic circuits 132 include a frequency generating circuit 200, a sensing circuit 202, a signal conditioning circuit 204, and a signal processing circuit 206. Each circuit is described below.

Frequency generating circuit 200 includes a plurality of frequency generators 208 which generate independent frequency signals 210, amplifiers 212 which amplify signals 210 to generate amplified frequency signals 214, a summing amplifier 216 which combines signals 214 to generate a combined frequency signal 218 having multiple frequency components, and a signal gain amplifier 220 which amplifies signal 218 to generate an amplified combined frequency signal 222. Signal 222 is the output signal from frequency generating circuit 200 which is applied to sensing circuit 202.

Preferably, each frequency generator 208 responds to its own control signal 224 to generate a frequency signal 210 having an adjustable frequency. Thus, each generator 208 can generate a frequency signal 210 having any of an unlimited number of frequencies. A number m (e.g., 4) of generators 208 generate m independent frequency signals 210 simultaneously, each of which is adjustable. Other numbers (e.g., 2, 3, etc.) of generators 208 may also be used. By increasing the number m of generators 208, the frequency response of material 110 to more frequencies can be determined simultaneously by circuit 132. Frequency generating circuit 200 could alternately include a white or pink noise generating circuit to generate a signal having many frequency components.

In one embodiment, generators 208 include digital frequency generator integrated circuits (ICs) to generate frequency signals in response to digital words written to the ICs as digital control signals 224. For example, generators 208 may include 10-bit numerically-controlled oscillators such as AD9850 devices available from Analog Devices. Voltage-controlled oscillator (VCO) circuits may also be used. FIG. 5 shows signals 210 as sinusoidal waves. Alternatively, other signals (e.g., square waves) may be used if no other signals are present at the signal harmonics. Because only the signals' primary frequency is of interest, the harmonics of non-sinusoidal signals can be identified and ignored in the power spectrum.

Amplifiers 212 condition frequency signals 210 to an appropriate level such that amplified signals 214 can be accurately combined by summing amplifier 216, and so as to minimize the power dissipation of sensor assembly 112. For example, even if summing amplifier 216 was capable of attaining the slew rate required for each individual signal, the slew rate required for the sum of the signals could exceed the maximum slew rate of summing amplifier 216, thereby causing distortion. To prevent distortion, the level of each signal is adjusted by amplifiers 212. Summing and signal gain amplifiers 216 and 220 sum and control the combined signal level of the signals. Amplifiers 216 and 220 can be combined into a single amplifier circuit. The gain and offset of amplifiers 212 and 220 can be adjusted by appropriate control signals 226 and 228, respectively. Although referenced by common reference numbers in FIG. 5, control signals 226 and 228 are controlled separately for each amplifier in electronic circuit 132 to optimize signal level and power requirements for each frequency.

Sensing circuit 202 receives amplified combined frequency signal 222 from frequency generating circuit 200 and applies excitation signals to sensor assembly 112. Signal 222 is applied to sensor 116 via conductor 134, and is applied to a buffer circuit 230 including a unity-gain amplifier 232 for driving sensor shield 118 with low impedance via conductor 136. Sensor 116 and sensor shield 118 are driven by a common source to negate capacitive effects between sensor 116 and sensor shield 118, thereby focusing the electric field produced by sensor 116 towards material 110 and away from reference plane 124, thereby increasing the sensitivity to material 110. Further, signal 222 is applied to compensation sensor 122 via conductor 140, and is applied to a buffer circuit 234 including a unity-gain amplifier 236 for driving compensation sensor shield 120 with low impedance via conductor 138. Sensing circuit 202 includes reference plane 124 which is coupled to ground via conductor 142. Output signals from sensing circuit 202 are applied to signal conditioning circuit 204 and include sensed signal 238 and compensation signal 240.

Signal conditioning circuit 204 includes a combined signal adjustment amplifier 242 to adjust the level of sensed signal 238. An amplified sensed signal 244 is generated by amplifier 242 and is applied to a plurality of band-pass filters (BPFs) 246. BPFs 246 filter signal 244, and selectively filter compensation signal 240, and apply the filtered signals 248 to a plurality of filtered signal adjustment amplifiers 250. The adjusted filtered signals 252 are digitized by a plurality of analog-to-digital converters (ADCs) 254 and the digitized values 256 are made available to signal processing circuit 206.

Combined signal adjustment amplifier 242 adjusts the level of sensed signal 238 to maintain signal strength and low impedance for the signal entering BPFs 246. BPFs 246 filter amplified sensed signal 244, and compensation signal 240, to ensure the Nyquist criterion is satisfied for the given conversion rates of ADCs 254. The Nyquist criterion requires that a digital signal be sampled at twice the highest frequency content of the signal. Thus, the upper cutoff frequency $f_{Hn}$ for the nth BPF 246 is set to a maximum of one half the conversion rate for that ADC 254. For example, for an ADC conversion rate of 200 KSamples/sec, the upper cutoff frequency for that BPF 246 is 200 KHz/2=100 KHz. The lower cutoff frequency $f_{Ln}$ can be arbitrarily defined. However, if the DC component of signal 244 is desired, the lower cutoff frequency is set to 0 Hz to make a low pass filter. If it is desired to exclude the DC component from the power spectrum, the lower cutoff frequency is set to a nominal value to eliminate the DC component of signal 244.

In one embodiment, the cutoff frequencies BPFs 246 and corresponding conversion rates of ADCs 254 are:

| | |
|---|---|
| BPF 1: f < 1 KHz | ADC 1: 2 KS/sec |
| BPF 2: 1 KHz < f < 100 KHz | ADC 2: 200 KS/sec |
| BPF n: $f_{Ln}$ Hz < f < $f_{Hn}$ | ADC n: 2*$f_{Hn}$ S/sec |

Filtered signal adjustment amplifiers 250 control the gain of the signals output from BPFs 246 to achieve maximum signal amplitude resolution given the finite resolution of ADCs 254. The gain and offset of amplifiers 242 and 250 can be adjusted by appropriate control signals 226 and 228, respectively. ADCs 254 convert the analog signals 252 into digital signals for use by signal processing circuit 206. As described above, the sampling rate of ADCs 254 is selected to be no less than twice the upper cutoff frequency of BPFs 246.

Signal processing circuit 206 includes memory storage devices 258 which store the digitized signals received from signal conditioning circuit 204, and a processing circuit 260 which processes the digitized signals to determine various parameters of material 110. Processing circuit 260 includes an interface 262 (e.g., RS-485, J-1939, or other analog or digital interface) for communication with an external system (not shown).

In one embodiment, memory storage devices 258 include dual-port RAMs (DPRs) and processing circuit 260 includes a digital signal processor (DSP). For example, the ADSP-21060-LBW-160X DSP available from Analog Devices may be used. However, other types of memory devices or processing circuits (e.g., other DSPs or microprocessors having sufficient throughput) may be used. The amount of memory in each device 258 depends on the conversion rate of ADCs 254 and the desired frequency resolution:

Memory (samples)=Conv Rate (Hz)/Freq. Res. (Hz)

For example, with a conversion rate of 2 KSample/sec and a desired frequency resolution of 0.5 Hz, memory storage device 258 for this frequency is required to store 4 KSamples. DRPs 1 and 2 in FIG. 5 each store 4 K samples.

Preferably, processing circuit 260 (i.e., the DSP) generates digital control signals 224 which are applied to generators 208, and generates gain and offset control signals 226 and 228 which are applied to amplifiers 212, 220, 242 and 250. Each control signal 226 and 228 is generated independently to optimize signal level and power requirements for each frequency. Each control signal 224 is also generated independently to select the frequencies of interest. Control signals 224 may depend on input signals from an external device (e.g., computer) coupled to interface 262. Thus, the external device may select the frequencies used to analyze material 110.

In another embodiment, any or all of generators 208 and amplifiers 212, 220, 242 and 250 are not adjustable, and the corresponding control signals are not needed.

Processing circuit 260 performs a frequency analysis on the digital signals stored in memory circuits 258 to determine the frequency characteristics of material 110. For example, processing circuit 260 generates a power spectrum by taking a Fourier transform of the digital signals. The power is determined as the square root of the sum of the real part squared and the imaginary part squared. The frequency characteristics are then used to identify various parameters of material 110 (e.g., mass flow rate; moisture content). The type of material and speed of the conveyor can also be determined. Because generators 208 are adjustable, any number of frequencies can be applied to sensor assembly 112 to determine the response of material 110 to any number of frequencies. Thus, a desired resolution can be achieved over a wide frequency range without requiring an impractically high number of fixed frequency sources.

Processing circuit 260 is configured to determine the power spectrum of sensed signal 238 by combining the power spectrums from the data acquired by each ADC 254. The power spectrum is then used to determine parameters of material 110 being measured. By using multiple BPFs 246 and ADCs 254, higher resolutions can be achieved at lower frequencies while still providing a power spectrum for a high bandwidth. Moreover, since the frequencies of interest are known, processing circuit 260 can also be configured to process only part of the power spectrum to obtain data only for the frequencies of interest. The partial power spectrum will eliminate the effects of any noise at other frequencies that are not of interest.

In one embodiment, processing circuit 260 determines the mass flow rate and moisture content of material 110 by applying the signals stored in memory circuits 258 to pre-determined processing algorithms. One or both of these parameters may be determined because the relative sensitivity of sensor assembly 112 to the mass flow rate and moisture content differ at different frequencies. A test and calibration process may be used to determine the algorithms. For example, the apparatus may be calibrated by recording test data detected by sensor assembly 112 as material is moved through auger 100 and comparing such test data to independently sensed or known mass flow rate and moisture content data. The test and known data may be input to a computer which is programmed to execute a curve-fit algorithm or statistical analysis package to curve fit the data. A neural network with a learning algorithm may also be used.

In one embodiment, processing circuit 260 executes a multiple linear regression algorithm to determine mass flow rate and moisture content using the equations:

mass flow rate=$a_0+a_1f_1+a_2f_2=\ldots+a_nf_n$ moisture content=$b_0+b_1f_1+b_2f_2+\ldots+b_nf_n$ wherein $a_1$ and $b_1$ are coefficients and $f_1$ are various frequencies. Coefficient values are determined using a calibration process and curve-fit algorithm as described above. Of course, a measuring apparatus such as that described herein may also be configured to detect only one parameter. The mass flow rate may be in units of kg/sec, and processing circuit 260 may accumulate or integrate mass flow rate to determine the total mass. Data generated from compensation signal 240 can be used to correct the parameters for environmental variations.

Processing circuit 260 may also be configured to determine the type of material based upon the sensor output in response to excitation signals of different frequencies. Thus, for example, processing circuit 260 may process the detected signals to distinguish between different types or varieties of grain. A calibration and testing process may be used to determine the algorithms used by processing circuit 260 to determine the type.

Processing circuit 260 may be configured to correct the calculated parameters for the effects of the rotation of auger screw 104. The sensitivity of sensor 116 to the rotation of screw 104 may be affected by the completeness of the ring around tube 102. When sensor 116 makes a complete ring, sensor assembly 112 may show little or no sensitivity to rotations of screw 104, although variances in auger 100 may cause some sensitivity. However, when sensor 112 makes an incomplete ring, as shown in FIG. 3, the sensitivity may increase. To correct for the quasi-sinusoidal effect on the capacitance value of sensor assembly 112 as screw 104 rotates, a hardware filter may be used, or processing circuit 260 may be programmed to filter the input data. For example, circuit 260 may be programmed to average data over time, or to time sample the data such that the auger position is consistent. Similarly, processing circuit 260 may be configured to eliminate the effect of paddles 158 of an elevator.

Processing circuit 260 may also be configured to determine the rate of rotation of auger screw 104. As screw 104 rotates, a quasi-sinusoidal signal or wave will be imposed on sensed signal 238. To determine auger speed, processing circuit 260 may process the signal using a Fourier transform to determine a power spectrum, or the sensed signals may be conditioned with a high-pass filter and the frequency of the filtered signal measured using a comparator, counter circuit, or other techniques. Similarly, processing circuit 260 may be configured to determine the operating speed of elevator conveyor 150. The velocity of material being conveyed by a pneumatic conveyor can be determined by measuring the fan speed and applying empirically-determined relationships between fan speed and air velocity. Fan speed can be measured, for example, using a rotational sensor coupled to the shaft driving the fan.

In one embodiment, a temperature sensor 264 is coupled to (i.e., attached to or embedded in) sensor assembly 112 to measure the temperature of the probe and to generate a temperature signal 266 read by processing circuit 260 through a signal conditioning circuit 268 which can include an A/D circuit. Temperature signal 266 is used by processing circuit 260 to temperature compensate the sensed signals. Temperature sensor 264 may include a thermocouple.

Electronic circuits 132 may be located in any suitable location on the particular conveyor system, and may be separated into several electronic packages. For example, circuits 132 could be attached to auger 100, or the electronics which drive sensor assembly 112 could be located at the auger and the processing electronics could be located elsewhere. Processing circuit 260 can be part of another electronics package, such as a data processing unit on a combine, which performs other functions.

Figure 6A:
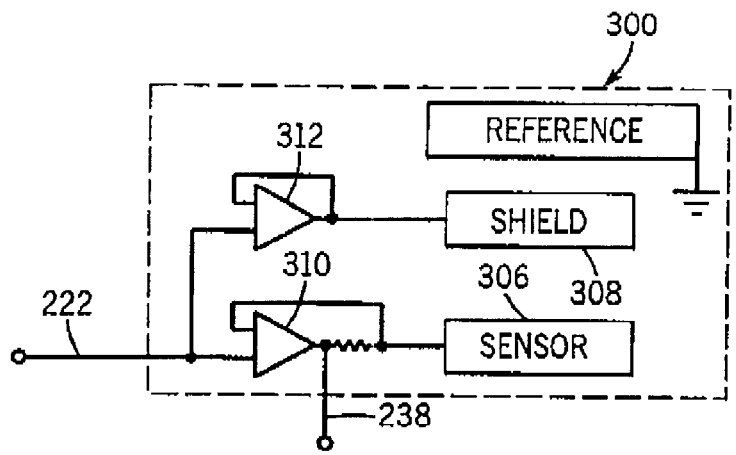
FIGS. 6A–6C are electrical schematic diagrams which represent alternative embodiments of the sensor assembly shown in FIG. 5.
Figure 6B:
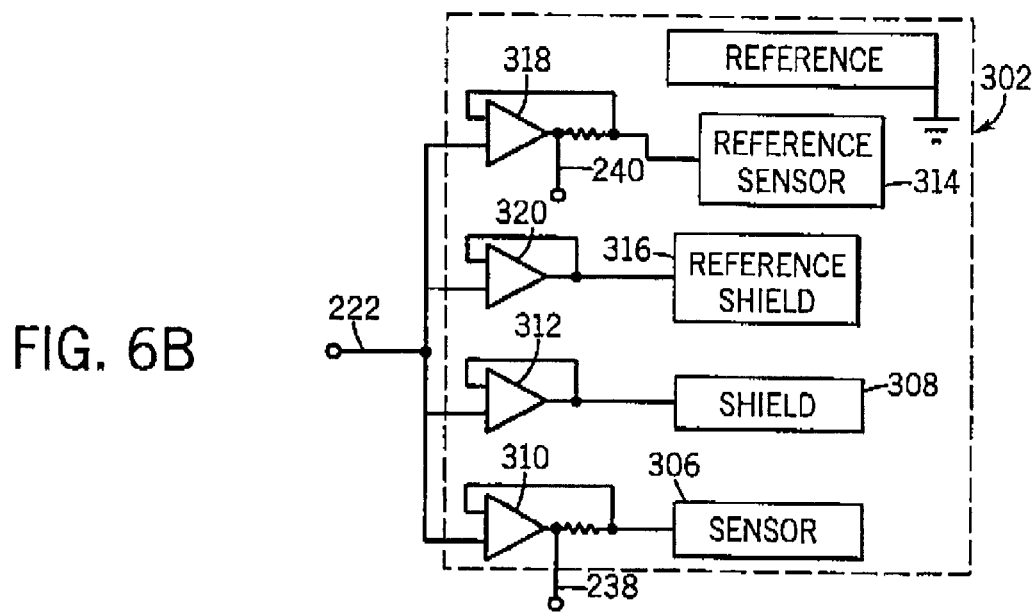
Figure 6C:
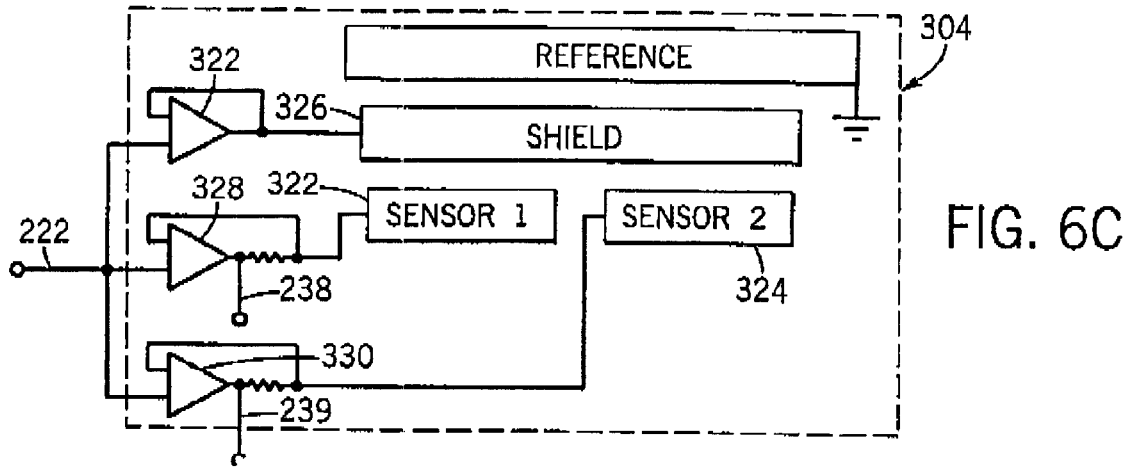

Referring to FIG. 6, three alternative sensing circuits 300, 302 and 304 which include capaciflector sensing elements are shown. In FIG. 6A, sensing circuit 300 includes a sensor 306 and a sensor shield 308 which are driven by combined frequency signal 222 via amplifiers 310 and 312, respectively. In FIG. 6B, sensing circuit 302 further includes a reference probe including reference sensor 314 and reference shield 316, which are also driven by signal 222 via amplifiers 318 and 320, respectively. In FIG. 6C, sensing circuit 304 includes two sensor probes 322 and 324 and a common sensor shield 326 for both sensor probes. Probes 322 and 324, and sensor shield 326, are driven by signal 222 via amplifiers 328–332, respectively. Probes 322 and 324 are preferably positioned at locations having differing relationships with the material being measured such that the sensitivity of the probes differ with respect to the parameters being measured. For example, probe 322 could be located along a side or bottom of an auger tube, and probe 324 could be located around the circumference of the auger tube.

Figure 7:
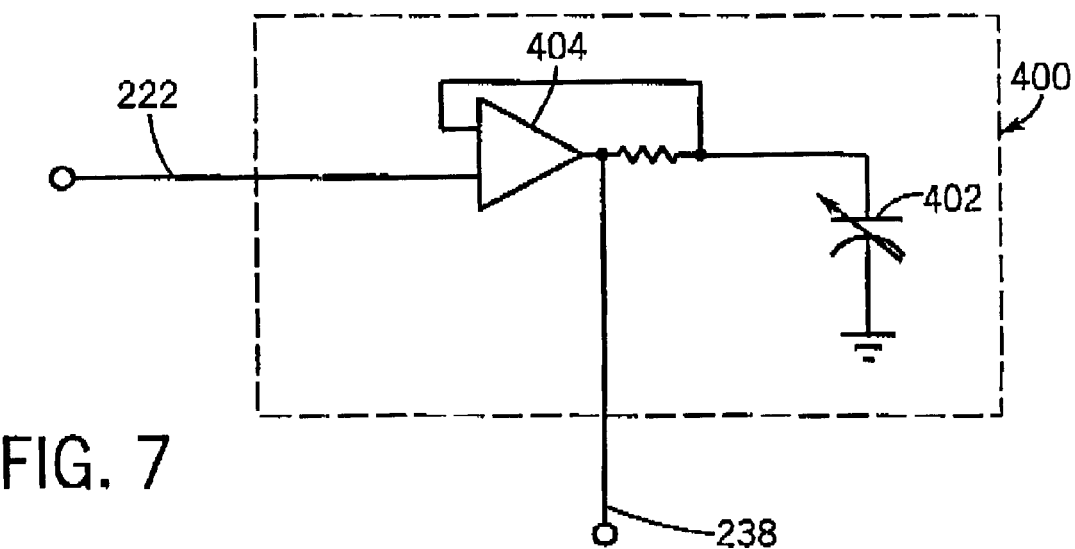
FIG. 7 is an electrical schematic diagram which represents an alternative sensor assembly including a capacitive sensing element.

The electronic circuits of FIG. 5 may also be coupled to other types of sensing elements to measure the frequency response of such sensing elements over a range of frequencies. For example, in FIG. 7, a sensing circuit 400 includes a capacitive sensing element 402 also driven by signal 222 via amplifier 404. Sensing element 402 may form part of, for example, a capacitive cell which receives material to be tested. The cell can include a central cylindrical electrode and an outer concentric electrode configured to measure the dielectric of material placed between the central and the outer electrodes. In addition, the electronic circuits can be used to measure the frequency response of resistive or inductive sensing elements. For example, a resistive sensing element can be used to measure soil parameters (e.g., soil type, soil moisture content) by measuring soil resistance at different frequencies. Further, the electronic circuits can be used to measure both conductive and capacitive frequency response. The complex frequency response can be used, for example, to identify and analyze materials using various testing devices.

While the embodiments illustrated in the FIGURES and described above are presently preferred, it should be understood that these embodiments are offered by way of example only. The invention is not intended to be limited to any particular embodiment, but is intended to extend to various modifications that nevertheless fall within the scope of the appended claims.

What is claimed is:

1. A work vehicle, comprising:
   a support structure for supporting components of the work vehicle;
   a plurality of wheels coupled to the support structure to move the work vehicle on a surface, at least one of the wheels being powered to move the work vehicle along the surface;
   at least one conveyor to move material from a first location to a second location on the work vehicle;
   a frequency generating circuit configured to generate a combined frequency signal having a plurality of frequency components selected in response to a plurality of frequency control signals;

a sensing circuit coupled to the frequency generating circuit and including a sensing element coupled to the at least one conveyor, wherein the combined frequency signal is applied as an excitation signal to the sensing element and the sensing element generates output signals based upon the frequency response of the material being moved at each of the frequencies;

a signal conditioning circuit coupled to the sensing circuit and configured to determine the frequency response of the material at each of the frequencies based upon the output signals from the sensing element; and a signal processing circuit configured to analyze the frequency response of the material to determine the at least one parameter of material.

2. The work vehicle of claim 1 wherein the sensing element includes a capaciflector sensor assembly.

3. The work vehicle of claim 2 wherein the capaciflector sensor assembly is non-intrusively mounted along a surface of said at least one conveyor configured to move the material being measured.

4. The work vehicle of claim 3 wherein the conveyor is selected from the group consisting of an auger, an elevator and a pneumatic delivery system.

* * * * *